United States Patent
Machida et al.

(10) Patent No.: US 10,202,337 B2
(45) Date of Patent: Feb. 12, 2019

(54) METHOD FOR PRODUCING TRI-CARBOBENZOXY-ARGININE

(71) Applicant: KANEKA CORPORATION, Osaka (JP)

(72) Inventors: Koji Machida, Takasago (JP); Kohei Mori, Takasago (JP); Narumi Kishimoto, Takasago (JP); Toshihiro Takeda, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 15/129,927

(22) PCT Filed: Mar. 23, 2015

(86) PCT No.: PCT/JP2015/058672
§ 371 (c)(1),
(2) Date: Sep. 28, 2016

(87) PCT Pub. No.: WO2015/146882
PCT Pub. Date: Oct. 1, 2015

(65) Prior Publication Data
US 2017/0174622 A1    Jun. 22, 2017

(30) Foreign Application Priority Data
Mar. 28, 2014 (JP) .................. 2014-068838

(51) Int. Cl.
C07C 277/08    (2006.01)

(52) U.S. Cl.
CPC .................. *C07C 277/08* (2013.01)

(58) Field of Classification Search
None
See application file for complete search history.

(56) References Cited

U.S. PATENT DOCUMENTS

| | | | |
|---|---|---|---|
| 3,856,848 A | 12/1974 | Smithwick, Jr. | |
| 2005/0176999 A1 | 8/2005 | Yamashita et al. | |
| 2010/0004450 A1 | 1/2010 | Cesco-Cancian et al. | |
| 2013/0053561 A1 | 2/2013 | Cesco-Cancian et al. | |
| 2013/0225816 A1 | 8/2013 | Cesco-Cancian et al. | |
| 2014/0066624 A1 | 3/2014 | Cesco-Cancian et al. | |
| 2014/0073795 A1 | 3/2014 | Cesco-Cancian et al. | |
| 2014/0121374 A1 | 5/2014 | Cesco-Cancian et al. | |

FOREIGN PATENT DOCUMENTS

| | | |
|---|---|---|
| CN | 1282731 A | 2/2001 |
| JP | 11-71335 A | 3/1999 |
| JP | 2001-199943 A | 7/2001 |
| JP | 2002-173457 A | 6/2002 |
| JP | 2003-300926 A | 10/2003 |
| JP | 2011-526910 A | 10/2011 |
| WO | WO 03/066563 A1 | 8/2003 |

OTHER PUBLICATIONS

International Search Report dated Jun. 9, 2015 in PCT/JP2015/058672, filed Mar. 23, 2015.
Mieke Jetten et al. "A One-Pot N-Protection of L-Arginine.", Tetrahedron Letters, vol. 32, No. 42, 1991, pp. 6025-6028.
Leonidas Zervas et al. "Studies on Arginine Peptides. I. Intermediates in the Synthesis of N-Terminal and C-Terminal Arginine Peptides", Studies on Arginine Peptides, vol. 22, No. 11, Nov. 1957, pp. 1515-1521.
Extended European Search Report dated Sep. 28, 2017 in Patent Application No. 15769421.7.
Jiacai Feng, et al. "Research on synthetic methods of Cbz protected RGD-OH", Hebei Keji Daxue Xuebao, Journal of Hebei University of Science and Technology, vol. 34, No. 5. XP055403901, 2013. pp. 430-433 (with English abstract).
Humphrey A. Moynihan. et al. "Alkoxycarbonylation and Selective Deprotection of N-Silyl Derivatives of L-Arginine", Tetrahedron Letters. Elsevier. vol. 39, No. 20, XP004116270, 1998. pp. 3349-3352.
Edward L. Smithwick Jr., et al. "A New Synthesis $N^\alpha$, $N^{G,G}$-Tribenzyloxycarbonyl-L-arginine and Related Derivatives", The Journal of Organic Chemistry, vol. 39, No. 23, XP055403800, 1974, pp. 3441-3442.

*Primary Examiner* — Clinton A Brooks
(74) *Attorney, Agent, or Firm* — Oblon, McClelland, Maier & Neustadt, L.L.P.

(57) ABSTRACT

A tri-carbobenzoxy-arginine represented by the following formula (2):

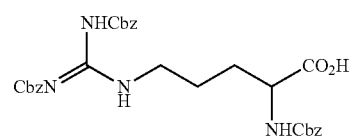

(2)

is produced by carbobenzoxylating the arginine or arginine derivative (1) represented by the following formula (1), or a salt thereof:

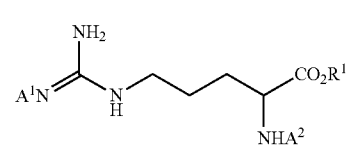

(1)

by adding carbobenzoxy chloride and a base in a water/organic solvent bilayer system to an arginine or arginine derivative (1) represented by the formula (1), or a salt thereof.

14 Claims, No Drawings

METHOD FOR PRODUCING TRI-CARBOBENZOXY-ARGININE

TECHNICAL FIELD

The present invention relates to a method for producing a tri-carbobenzoxy-arginine useful for production of peptides.

BACKGROUND ART

Amino acids in which amino groups or carboxyl groups are protected with protecting groups are commonly used in production of pharmaceutical bulk drugs and intermediates such as peptides. A tri-carbobenzoxy-arginine is one of important raw material compounds in production of a peptide comprising an arginine as a component.

A method for obtaining a tri-carbobenzoxy-arginine has been reported in which a commercially available arginine is dissolved in an aqueous NaOH solution, and reacted by adding carbobenzoxy chloride and NaOH to convert the arginine into a tri-carbobenzoxy-arginine sodium salt, thereafter filtration is performed to obtain the tri-carbobenzoxy-arginine sodium salt, the tri-carbobenzoxy-arginine sodium salt is neutralized using sulfuric acid, and then extracted with ethyl acetate to synthesize a tri-carbobenzoxy-arginine (Non-Patent Document 1).

However, in the above-mentioned method, a solid is precipitated in an aggregated form in the middle stage of the reaction, so that handling is difficult for production on an industrial scale. In addition, in the above-mentioned method, a di-carbobenzoxy-arginine remains at the end of the reaction, and therefore the yield is markedly reduced. Further, in the above-mentioned method, filtration of the tri-carbobenzoxy-arginine sodium salt is performed several times, but the filtration characteristic is very poor. Thus, the method has a major problem in production on an industrial scale.

PRIOR ART DOCUMENT

Non-Patent Document

Non-Patent Document 1: J. Org. Chem., 1957, 22(11), 1515-1521

SUMMARY OF THE INVENTION

Problems to be Solved by the Invention

In view of the problems of the conventional techniques, an object to be achieved by the present invention is to provide a method capable of efficiently producing a high-purity tri-carbobenzoxy-arginine on an industrial scale.

Solutions to the Problems

The present inventors have extensively conducted studies, and resultantly found that when a reaction for tri-carbobenzoxylating by causing carbobenzoxy chloride to act on the arginine using a base is carried out in a water/organic solvent bilayer system using an organic solvent in addition to water as a conventional reaction solvent, the reaction liquid has satisfactory fluidity, leading to achievement of a method capable of producing a tri-carbobenzoxy-arginine on an industrial scale.

The present inventors have also found that when the obtained tri-carbobenzoxy-arginine forms a salt with dicyclohexylamine, the tri-carbobenzoxy-arginine can be obtained as a solid having a satisfactory filtration characteristic, and can be obtained as a high-purity tri-carbobenzoxy-arginine amine salt.

The present inventors have also found that when an acid is added to the obtained tri-carbobenzoxy-arginine amine salt to extract the tri-carbobenzoxy-arginine in an organic layer, a high-purity tri-carbobenzoxy-arginine can be obtained.

That is, the present invention relates to a method for producing a tri-carbobenzoxy-arginine, comprising adding carbobenzoxy chloride and a base in a water/organic solvent bilayer system to an arginine or arginine derivative (1) represented by the following formula (1), or a salt thereof:

[Chemical Formula 1]

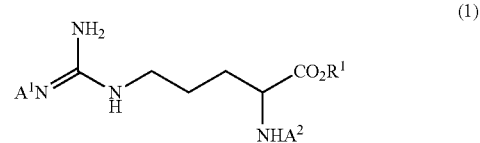

(1)

wherein $A^1$ and $A^2$ each represent an amino group protecting group or a hydrogen atom; and $R^1$ represents a hydrogen atom, an alkyl group having 1 to 6 carbon atoms optionally having a substituent, or an aralkyl group having 7 to 15 carbon atoms optionally having a substituent, to carbobenzoxylate the arginine or arginine derivative (1) represented by the formula (1), or a salt thereof, wherein, the tri-carbobenzoxy-arginine is represented by the following formula (2):

[Chemical Formula 2]

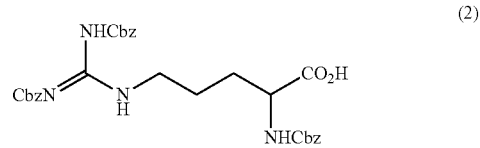

(2)

wherein Cbz represents a benzyloxycarbonyl group.

It is preferable that in the carbobenzoxylation step, the addition of carbobenzoxy chloride and the base in a bilayer system is carried out in the presence of a surfactant. The base is preferably an alkali metal hydroxide, the compound represented by the formula (1) is preferably an arginine or arginine hydrochloride. It is preferable that the method further comprising deprotecting and carbobenzoxylating the amino group protecting group represented by $A^1$ or $A^2$, in case where $A^1$ or $A^2$ is an amino protecting group.

Further, the present invention relates to a tri-carbobenzoxy-arginine amine salt represented by the following formula (3):

[Chemical Formula 3]

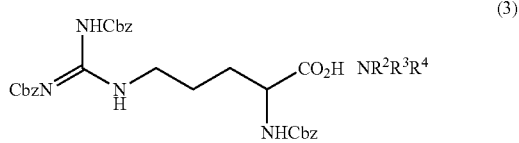

(3)

wherein $R^2$, $R^3$ and $R^4$ each represent a hydrogen atom, an alkyl group having 1 to 6 carbon atoms optionally having a substituent, or an aralkyl group having 7 to 15 carbon atoms optionally having a substituent.

Further, the present invention relates to a method for producing a tri-carbobenzoxy-arginine amine salt as a solid, comprising adding an amine to a tri-carbobenzoxy-arginine represented by the following formula (2):

[Chemical Formula 4]

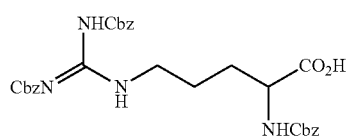

(2)

to obtain the tri-carbobenzoxy-arginine amine salt represented by the following formula (3):

[Chemical Formula 5]

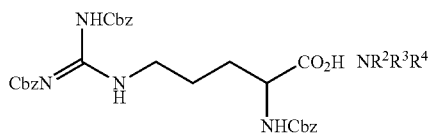

(3)

wherein $R^2$, $R^3$ and $R^4$ represent the same groups as the above.

Further, the present invention relates to a method for producing a tri-carbobenzoxy-arginine amine with high purity, comprising adding an acid to the obtained tri-carbobenzoxy-arginine amine salt to extract a tri-carbobenzoxy-arginine in an organic layer.

Effects of the Invention

According to the present invention, the reaction liquid has satisfactory fluidity, so that a tri-carbobenzoxy-arginine can be efficiently produced on an industrial scale. When the tri-carbobenzoxy-arginine forms a salt with an amine, a tri-carbobenzoxy-arginine amine salt can be obtained as a solid having a satisfactory filtration characteristic, and further, when the tri-carbobenzoxy-arginine is extracted in an organic layer under an acidic condition, a high-purity tri-carbobenzoxy-arginine can be efficiently and conveniently produced on an industrial scale.

MODE FOR CARRYING OUT THE INVENTION

Hereinafter, a method according to the present invention will be described in detail. While the present invention will be described in detail below with reference to an arginine or arginine derivative (1) and a tri-carbobenzoxy-arginine (2), these compounds have tautomers. In this specification, some examples of the tautomers are employed, and explained as formulae (1) and (2), respectively, but the formulae (1) and (2) include the following tautomers in addition to those represented by these formulae.

[Chemical Formula 6]

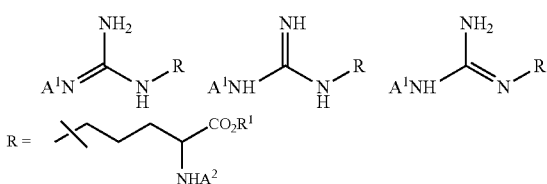

[Chemical Formula 7]

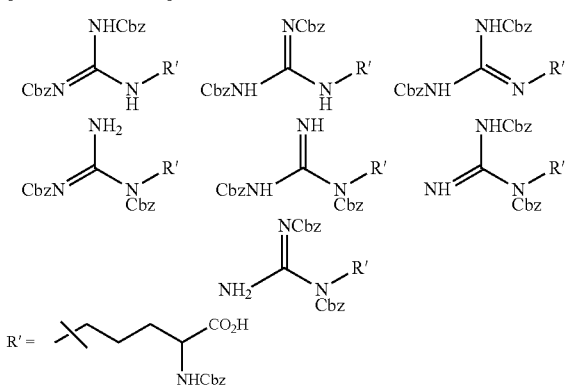

<Carbobenzoxylation>

[Chemical Formula 8]

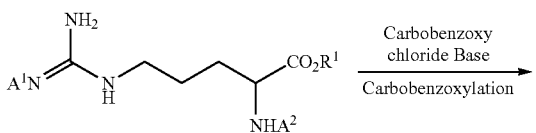

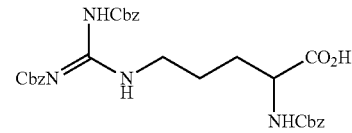

In the present invention, carbobenzoxy chloride and a base are added to an arginine or arginine derivative of formula (1), or a salt thereof (hereinafter, collectively referred to as an arginine raw material (1)) in a water/organic solvent bilayer system to perform carbobenzoxylation while maintaining excellent fluidity of a reaction liquid capable of enduring production on an industrial scale. The resulting tri-carbobenzoxy-arginine is a carboxylic acid salt, and by, for example, extracting the salt with an organic solvent under an acidic condition, a salt-free product of tri-carbobenzoxy-arginine can be produced. It is preferable that a surfactant exists in the carbobenzoxylation, so that a di-carbobenzoxy-arginine can be efficiently converted into a tri-carbobenzoxy-arginine, leading to a considerable increase in yield.

In the formula (1), $A^1$ and $A^2$ each represent a N protecting group (an amino group protecting group) or a hydrogen atom. The amino group protecting group is selected normally from known amino protecting groups other than a benzyloxycarbonyl group, and examples thereof may include acyl-type protecting groups such as a formyl group, an acetyl group, a trifluoroacetyl group, a benzoyl group, a pivaloyl group and a phthaloyl group; urethane-type (carbamate-type) protecting groups such as a carbobenzoxy group, a t-butoxycarbonyl group, an isopropoxycarbonyl group, an ethoxycarbonyl group and a methoxycarbonyl group; substituted alkyl groups such as a benzyl group, a p-methoxybenzyl group and a triphenylmethyl group; a p-toluenesulfonyl group, a benzenesulfonyl group, a trifluoromethanesulfonyl group, a t-butyldimethylsilyl group, a t-butyldiphenylsilyl group and a triphenylsilyl group.

Preferably, $A^1$ and $A^2$ are each a hydrogen atom. When $A^1$ and $A^2$ are each a N protecting group, it is preferable to perform carbobenzoxylation after deprotecting the N protecting group.

In the above formula, $R^1$ represents a hydrogen atom, an alkyl group having 1 to 6 carbon atoms optionally having a substituent, or an aralkyl group having 7 to 15 carbon atoms optionally having a substituent. Preferably, $R^1$ is a hydrogen atom.

Examples of the alkyl group include a methyl group and an ethyl group, and examples of the aralkyl group include a benzyl group and a phenethyl group.

The arginine raw material (1) may be a racemic modification, or an optically active substance showing optical rotation.

The arginine raw material (1) may be a salt with an acid. Examples of the acid include mineral acids, sulfonic acids and carboxylic acids. The mineral acid is not particularly limited, and examples thereof include acids comprising hydrogen halides such as hydrogen chloride and hydrogen bromide (hydrochloric acid, hydrobromic acid and the like), sulfuric acid and phosphoric acid. The sulfonic acid is not particularly limited, and examples thereof include methanesulfonic acid, ethanesulfonic acid, propanesulfonic acid, butanesulfonic acid, benzenesulfonic acid, p-toluenesulfonic acid, camphorsulfonic acid and 1-phenylethanesulfonic acid. The carboxylic acid is not particularly limited, and examples thereof include non-optically-active carboxylic acids such as formic acid, acetic acid, trifluoroacetic acid and benzoic acid, and optically active carboxylic acids such as tartaric acid. The acid is preferably a mineral acid, more preferably hydrochloric acid or sulfuric acid.

The arginine raw material (1) is preferably an arginine or arginine salt with $A^1$ and $A^2$ being each a hydrogen atom, more preferably an arginine or arginine hydrochloride.

The organic solvent to be used in the reaction is not particularly limited as long as it is a solvent which forms a bilayer system with water during the reaction, and is capable of maintaining fluidity of a reaction liquid. The organic solvent may be a solvent which is layer-separated from water in a solute-free state, and a solvent which can be freely mixed with water at any ratio as long as the solvent is in a solute-free state. The solvent is preferably one in which the resulting tri-carbobenzoxy-arginine is precipitated, and released to the outside of the system, and examples thereof include acetic acid esters such as ethyl acetate, n-propyl acetate, isopropyl acetate, n-butyl acetate, isobutyl acetate and tert-butyl acetate; ethers such as tert-butyl methyl ether and ethylene glycol dibutyl ether; halogenated hydrocarbons such as dichloromethane, chloroform and 1,2-dichloroethane; and aromatic hydrocarbons such as toluene, chlorobenzene and xylene. Among them, tert-butyl methyl ether, dichloromethane and toluene are preferable. It is needless to say that these organic solvents may be used alone, or used in combination of two or more thereof.

The amount of the organic solvent to be used in the reaction solvent is not particularly limited, but for example, it is not more than 32 parts by weight, preferably not more than 16 parts by weight, more preferably not more than 8 parts by weight with respect to 1 part by weight of the arginine raw material (1). The lower limit of the amount of the organic solvent is not particularly limited, but for example, it is not less than 1 part by weight, preferably not less than 2 parts by weight, more preferably not less than 4 parts by weight.

The amount of water to be used in the reaction is not less than 1 part by weight, preferably not less than 2 parts by weight, more preferably not less than 3 parts by weight with respect to 1 part by weight of the organic solvent. The upper limit of the amount of water is not particularly limited, but for example, it is not more than 10 parts by weight, preferably not more than 8 parts by weight, more preferably not more than 6 parts by weight. When the amount of water is to be set, the origin of water does not matter, and all water existing during the reaction, including not only water added as water but also water used for dissolving the base, etc. is taken into consideration. When the amount of water changes as the reaction proceeds, for example when the base is sequentially added, it is preferable to satisfy the above-mentioned amount of water at both the start of the reaction (at the time of adding carbobenzoxy chloride) and the end of the reaction.

The temperature in the reaction is not particularly limited as long as it is a temperature that is high enough to prevent the reaction solvent from being solidified, but the temperature in the reaction is not higher than 100° C., preferably not higher than 80° C., more preferably not higher than 50° C. The lower limit of the temperature is not lower than −50° C., preferably not lower than −30° C., more preferably not lower than −10° C.

The amount of the carbobenzoxy chloride is not particularly limited, but the upper limit thereof is not more than 32 mol, preferably not more than 16 mol, more preferably not more than 8 mol with respect to 1 mol of the arginine raw material (1). The lower limit of the amount of the carbobenzoxy chloride is not particularly limited, but for example, it is not less than 3 mol, preferably not less than 4 mol, more preferably not less than 4.3 mol with respect to 1 mol of the arginine when $A^1$ and $A^2$ are each a hydrogen atom in the above formula.

The base is not particularly limited, and may be either an organic base or an inorganic base. The base is preferably an inorganic base, and examples of the inorganic base include alkali metal and alkali earth metal-containing compounds such as alkali metal hydroxides, alkali metal carbonates, alkali metal hydrogen carbonates, alkali earth metal hydroxides, alkali earth metal carbonates, and alkali earth metal hydrogen carbonates. Specific examples of the inorganic base include lithium hydroxide, sodium hydroxide, potassium hydroxide, lithium carbonate, sodium carbonate, potassium carbonate, sodium hydrogen carbonate, potassium hydrogen carbonate, calcium hydroxide, calcium carbonate and calcium hydrogen carbonate. The inorganic base is preferably an alkali metal hydroxide, more preferably lithium hydroxide, sodium hydroxide or potassium hydroxide, further preferably sodium hydroxide or potassium hydroxide.

The amount of the base is not particularly limited, but it is not more than 36 parts by mol, preferably not more than 20 parts by mol, more preferably not more than 12 parts by mol with respect to 1 part by mol of the arginine or arginine derivative. When a salt of the arginine or arginine derivative is used as a raw material, it is necessary to neutralize the salt using the base, and therefore it is practical to add the base in an amount larger by 1 mol than the amount in a range as described above. The lower limit of the amount of the base is not particularly limited, but for example, when $A^1$, $A^2$ and R¹ in the above formula are each a hydrogen atom, the lower limit of the amount of the base is 4 parts by mol with respect to 1 mol of the arginine raw material (1) (preferably the arginine or arginine derivative) in consideration of the amount (1 part by mol) needed for neutralizing a carboxylic acid of the arginine and the amount (3 parts by mol) needed for neutralizing hydrochloric acid generated in tri-carbobenzoxylation.

The base may be added as an aqueous solution as necessary. The concentration of the base in the aqueous solution is not particularly limited, but it is not more than 80 wt %, preferably not more than 60 wt %, more preferably not more than 40 wt %. The lower limit of the concentration of the base is not particularly limited, but from the viewpoint of productivity, it is preferably such a concentration that the reaction liquid amount does not extremely increases, and it is 1 wt %, preferably 3 wt %, more preferably 5 wt %.

In the present invention, the method for adding the carbobenzoxy chloride and base is not particularly limited, and the arginine raw material (1) and a predetermined amount of the base may be charged, followed by adding carbobenzoxy chloride, or the base and carbobenzoxy chloride may be simultaneously added while the pH is adjusted for suppressing decomposition of carbobenzoxy chloride and suppressing byproduction of impurities. The pH is, for example, in a range of about 8 to 14, preferably about 9 to 13, more preferably about 10 to 12.

An especially preferable addition procedure includes an addition step of first preparing a raw material mixed liquid comprising the arginine raw material (1), a part of the base, an organic solvent and water, and then adding thereto the total of the rest of the base and the total of carbobenzoxy chloride. The amount of the base in the raw material mixed liquid is, for example, not less than 0.5 mol, preferably not less than 1.0 mol, more preferably not less than 1.5 mol, and is, for example, not more than 4 mol, preferably not more than 3 mol, more preferably not more than 2.5 mol with respect to 1 mol of the arginine raw material (1).

In the addition step, the base and carbobenzoxy chloride may be sequentially added, or continuously added. The base and carbobenzoxy chloride may be alternately added, or simultaneously added. Preferably, the base and carbobenzoxy chloride are simultaneously and continuously added.

The addition step may be carried out in two or more stages. For example, the addition step may be carried out in a first addition step for bonding two benzyloxycarbonyl groups (Cbz) to the arginine raw material (1) and a second addition step for further bonding one benzyloxycarbonyl group (Cbz), and the first addition step and the second addition step may be each carried out in a plurality of stages.

The addition amount of the base in the first addition step is, for example, not less than 2 mol, preferably not less than 3 mol, more preferably not less than 4 mol, and is, for example, not more than 15 mol, preferably not more than 12 mol, more preferably not more than 8 mol, further preferably not more than 6 mol, still further preferably not more than 5 mol with respect to 1 mol of the arginine raw material (1). The addition amount of carbobenzoxy chloride in the first addition step is, for example, not less than 2.5 mol, preferably not less than 3.0 mol, more preferably not less than 3.5 mol, and is, for example, not more than 10 mol, preferably not more than 8.0 mol, more preferably not more than 6.0 mol, further preferably not more than 5.0 mol with respect to 1 mol of the arginine raw material (1).

The ratio of a di-carbobenzoxy-arginine (hereinafter, referred to as a "disubstituted product") at the end of the first addition step is, for example, not less than 25%, preferably not less than 30%, more preferably not less than 35%, further preferably not less than 42%, and is, for example, not more than 70%, preferably not more than 60%, more preferably not more than 55% with respect to 100% of the total of a mono-carbobenzoxy-arginine (hereinafter, referred to as a "monosubstituted product"), the disubstituted product and a tri-carbobenzoxy-arginine (hereinafter, referred to as a "trisubstituted product").

The addition amount of the base in the second addition step is, for example, not less than 2.0 mol, preferably not less than 2.5 mol, more preferably not less than 2.8 mol, and is, for example, not more than 7.0 mol, preferably not more than 6.0 mol, more preferably not more than 5.0 mol, further preferably not more than 4.0 mol with respect to 1 mol of the arginine raw material (1). The addition amount of carbobenzoxy chloride in the first addition step is, for example, not less than 1.0 mol, preferably not less than 1.5 mol, more preferably not less than 1.8 mol, and is, for example, not more than 4.0 mol, preferably not more than 3.5 mol, more preferably not more than 3.0 mol with respect to 1 mol of the arginine raw material (1).

It is preferable that in the second addition step, the addition amount of each of the base and carbobenzoxy chloride is smaller than the addition amount of each of the base and carbobenzoxy chloride in the first addition step, while the addition time is longer than that in the first addition step. The ratio of the addition time in the second addition step to the addition time in the first addition step is, for example, not less than 1, preferably not less than 2, more preferably not less than 2.5, and is, for example, not more than 10, preferably not more than 6, more preferably not more than 4.

The ratio of the trisubstituted product at the end of the second addition step is, for example, not less than 85%, preferably not less than 90%, more preferably not less than 92%, and is, for example, not more than 98%, preferably not more than 97%, more preferably not more than 96% with respect to 100% of the total of the monosubstituted product, the disubstituted product and the trisubstituted product. The ratio of the monosubstituted product at the end of the second addition step is, for example, not more than 5%, preferably not more than 3.5%, more preferably not more than 2% with respect to 100% of the total of the monosubstituted product, the disubstituted product and the trisubstituted product. The ratio of the disubstituted product at the end of the second addition step is, for example, not more than 10%, preferably not more than 8%, more preferably not more than 5%.

In the present invention, a surfactant may be added as necessary for improvement of the yield in the tri-carbobenzoxylation reaction. The surfactant is not particularly limited, and examples thereof may include carboxylic acid-type surfactants (particularly fatty acid-type surfactants having about 6 to 30 carbon atoms) such as sodium hexanoate, sodium heptanoate, sodium octanoate and sodium decanoate; sulfonic acid-type surfactants (particularly linear aliphatic sulfonic acid-type surfactants having about 6 to 30 carbon atoms) such as sodium 1-hexanesulfonate, sodium 1-heptanesulfonate, sodium 1-octanesulfonate, sodium 1-decanesulfonate and sodium 1-dodecanesulfonate; sulfuric acid ester-type surfactants (particularly sulfuric acid ester-type surfactants having a linear aliphatic hydrocarbon group having about 6 to 30 carbon atoms) such as sodium lauryl sulfate and ammonium lauryl sulfate; phosphoric acid ester-type surfactants (particularly phosphoric acid ester-type surfactants having a linear aliphatic hydrocarbon group having about 6 to 30 carbon atoms) such as lauryl phosphate, sodium lauryl phosphate and potassium lauryl phosphate;

quaternary ammonium salt-type surfactants such as tetrabutylammonium chloride, tetramethylammonium hydroxide and hexadecyltrimethylammonium bromide; alkylamine salt-type surfactants such as monomethylamine hydrochloride and trimethylamine hydrochloride; substances having a pyridine ring, such as butylpyridinium chloride and cetylpyridinium chloride; nonionic surfactants such as glycerin laurate and polyoxyethylene polyoxypropylene glycol; and amphoteric surfactants such as lauryl dimethylaminoacetic acid betaine and oleyl dimethylamine N-oxide. The surfactant is preferably a surfactant having a long-chain (linear) aliphatic hydrocarbon group having about 6 to 30 carbon atoms, more preferably a sulfonic acid-type surfactant.

The time at which the surfactant is used is not particularly limited as long as it is before completion of the reaction, but it is preferable that the surfactant exists in the reaction liquid at the start of the reaction (i.e., at the start of coexistence of the three components: arginine raw material (1), carbobenzoxy chloride and base), and it is especially preferable that the surfactant is included in the raw material mixed liquid.

The amount of the surfactant is not particularly limited, but it is not less than 0.01 parts by mol, preferably not less than 0.05 parts by mol, more preferably not less than 0.1 parts by mol with respect to 1 part by mol of the arginine raw material (1). The upper limit of the amount of the surfactant is not particularly limited, but it is 2 parts by mol, preferably 1 part by mol, more preferably 0.4 parts by mol with respect to 1 part by mol of the arginine raw material (1).

The tri-carbobenzoxy-arginine produced as described above is produced in a water/organic solvent system, and therefore is not aggregated, and is excellent in stirring characteristic, and also excellent in reaction selectivity or reaction yield. The reaction yield of the tri-carbobenzoxy-arginine is, for example, not less than 20%, preferably not less than 30%, more preferably not less than 45%. As the upper limit, a yield of 100% is desirable, but a yield of 80% is sufficiently high.

The obtained tri-carbobenzoxy-arginine may be isolated as necessary, or appropriately treated or refined while being kept in a solution or slurry state. Normally, the tri-carbobenzoxy-arginine forms a salt with a base (particularly an inorganic base) at the end of the reaction, and the salt is poor in filtration characteristic. Accordingly, it is preferable that the tri-carbobenzoxy-arginine is treated or refined while being kept in a solution or slurry state. Hereinafter, the case will be described where the tri-carbobenzoxy-arginine is treated or refined while being kept in a solution or slurry state.

When a reaction liquid comprising a salt of the tri-carbobenzoxy-arginine with a base (particularly an inorganic base) is, for example, treated with an acid, and then extracted with an organic solvent, inorganic impurities and water-soluble impurities can be removed, so that the purity of the tri-carbobenzoxy-arginine can be improved. The extraction after completion of the reaction may be performed with only an organic solvent and water used during the reaction, or water or an organic solvent may be appropriately added after completion of the reaction. The organic solvent to be added may be the same as or different from a solvent to be used in the reaction, and is not particularly limited. Examples of the organic solvent to be added include acetic acid esters such as ethyl acetate, n-propyl acetate, isopropyl acetate, n-butyl acetate, isobutyl acetate and tert-butyl acetate; ethers such as tert-butyl methyl ether and ethylene glycol dibutyl ether; halogenated hydrocarbons such as dichloromethane, chloroform and 1,2-dichloroethane; and aromatic hydrocarbons such as toluene, chlorobenzene and xylene. Among them, tert-butyl methyl ether, dichloromethane and toluene are preferable. It is needless to say that these organic solvents may be used alone, or used in combination of two or more thereof.

Examples of the acid to be used for acidification in extraction include mineral acids, sulfonic acids and carboxylic acids. The mineral acid is not particularly limited, and examples thereof include hydrogen halides such as hydrogen chloride and hydrogen bromide, sulfuric acid and phosphoric acid. The sulfonic acid is not particularly limited, and examples thereof include methanesulfonic acid, ethanesulfonic acid, propanesulfonic acid, butanesulfonic acid, benzenesulfonic acid, p-toluenesulfonic acid, camphorsulfonic acid and 1-phenylethanesulfonic acid. The carboxylic acid is not particularly limited, and examples thereof include non-optically-active carboxylic acids such as formic acid, acetic acid, trifluoroacetic acid and benzoic acid, and optically active carboxylic acids such as tartaric acid. Among these acids, preferable are hydrogen chloride, hydrogen bromide, sulfuric acid, p-toluenesulfonic acid and benzoic acid, particularly hydrogen chloride, hydrogen bromide and sulfuric acid, with hydrogen chloride and sulfuric acid being especially preferable.

The amount of the acid is not particularly limited as long as the pH can be adjusted to, for example, not more than 1.5 so that the tri-carbobenzoxy-arginine as a target can be extracted in an organic layer.

The extraction temperature is not particularly limited, and the extraction can be performed at a temperature that is high enough to prevent the reaction solvent from being solidified. The upper limit of the extraction temperature is 100° C., preferably 80° C., more preferably 50° C. The lower limit of the extraction temperature is not particularly limited, but it is −50° C., preferably −30° C., more preferably −10° C.

<Production of Tri-Carbobenzoxy-Arginine Amine Salt>

[Chemical Formula 9]

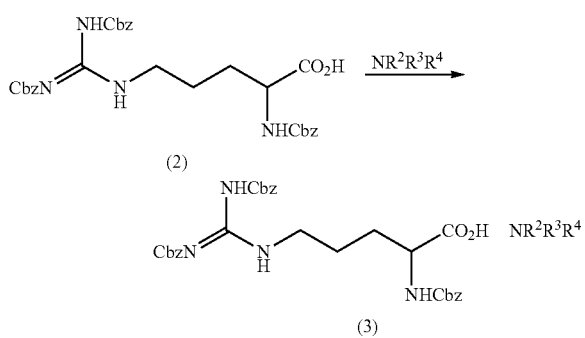

The present invention is characterized in that a tri-carbobenzoxy-arginine amine salt is produced by adding an amine to a tri-carbobenzoxy-arginine solution to solidify, and filtering the obtained solid. When an amine is added to the tri-carbobenzoxy-arginine solution to solidify, the obtained solid has a remarkably satisfactory filtration characteristic, so that refinement efficiency can be improved. The tri-carbobenzoxy-arginine to be used may be one obtained by the above-mentioned method, or may be one synthesized separately. The tri-carbobenzoxy-arginine solution may be a liquid obtained by adjusting the pH of a reaction liquid of a tri-carbobenzoxylated arginine to form a tri-carbobenzoxyarginine solution, or may be an extract obtained by extracting the liquid, or may be a solution prepared separately.

The tri-carbobenzoxy-arginine solution is normally an organic solvent solution. The organic solvent is not particularly limited, and examples of the organic solvent include acetic acid esters such as ethyl acetate, n-propyl acetate, isopropyl acetate, n-butyl acetate, isobutyl acetate and tert-butyl acetate; ethers such as tetrahydrofuran, 1,4-dioxane, tert-butyl methyl ether and ethylene glycol dibutyl ether; halogenated hydrocarbons such as dichloromethane, chloroform and 1,2-dichloroethane; aromatic hydrocarbons such as toluene, chlorobenzene and xylene; amides such as N,N-dimethylformamide; and nitriles such as acetonitrile. Tert-butyl methyl ether, dichloromethane, toluene, ethyl acetate and tetrahydrofuran are preferable. It is needless to say that these organic solvents may be used alone, or used in combination of two or more thereof. A tri-carbobenzoxy-arginine extract obtained by the above-mentioned method may be used.

The amount of the organic solvent is not particularly limited, but the upper limit thereof is 120 parts by weight, preferably 60 parts by weight, more preferably 30 parts by weight with respect to 1 part by weight of the tri-carbobenzoxy-arginine. The lower limit of the amount of the organic solvent is not particularly limited, and the organic solvent can be used in such an amount that the fluidity of the reaction liquid can be secured. The lower limit of the amount of the organic solvent is 2 parts by weight, preferably 5 parts by weight, more preferably 10 parts by weight with respect to 1 part by weight of the tri-carbobenzoxy-arginine.

$R^2$, $R^3$ and $R^4$ in the above general formula each independently represent a hydrogen atom, an alkyl group having 1 to 6 carbon atoms optionally having a substituent, or an aralkyl group having 7 to 15 carbon atoms optionally having a substituent. The alkyl group having 1 to 6 carbon atoms is not particularly limited, and examples thereof may include a methyl group, an ethyl group, a n-propyl group, an isopropyl group, a cyclopropyl group, a n-butyl group, a sec-butyl group, a tert-butyl group, a cyclobutyl group, a n-pentyl group, a cyclopentyl group, a n-hexyl group and a cyclohexyl group, with cycloalkyl groups such as a cyclohexyl group being preferable. The substituent is not particularly limited, and examples thereof may include alkyl groups such as a methyl group and an ethyl group, halogen atoms, an amino group and a hydroxyl group. Examples of the aralkyl group having 7 to 15 carbon atoms optionally having a substituent include a benzyl group, a p-chlorobenzyl group, a p-hydroxybenzyl group, a p-fluorobenzyl group, a m,m-difluorobenzyl group, a phenylethyl group and a naphthyl group.

The combination of $R^2$, $R^3$ and $R^4$ is preferably a combination in which $NR^2R^3R^4$ is a secondary amine, more preferably a combination in which any one of $R^2$, $R^3$ and $R^4$ is hydrogen, and the others are cycloalkyl groups such as a cyclohexyl group.

The amount of the amine is not particularly limited, but for securing the yield, it is necessary that the carboxylic acid of the tri-carbobenzoxy-arginine form an amine salt, and the amount of the amine is not less than 0.25 mol, preferably not less than 0.5 mol, more preferably not less than 1 mol with respect to 1 mol of the tri-carbobenzoxy-arginine. The upper limit of the amount of the amine is not limited, but it is not more than 8 mol, preferably not more than 4 mol, more preferably not more than 2 mol with respect to 1 mol of the tri-carbobenzoxy-arginine.

Solidification can be performed at a temperature that is high enough to prevent the reaction solvent from being solidified. The upper limit of the temperature for solidification is not particularly limited, but it is 100° C., preferably 70° C., more preferably 50° C. The lower limit of the extraction temperature is not particularly limited, but it is −50° C., preferably −30° C., more preferably −10° C.

Aging may be performed as necessary after the solidification. Solidification and aging are performed under stirring, and the stirring intensity per unit volume is not particularly limited, and is, for example, not less than 0.05 kW/m$^3$, more preferably not less than 0.1 kW/m$^3$, more preferably not less than 0.2 kW/m$^3$.

<Production of Tri-Carbobenzoxy-Arginine>

[Chemical Formula 10]

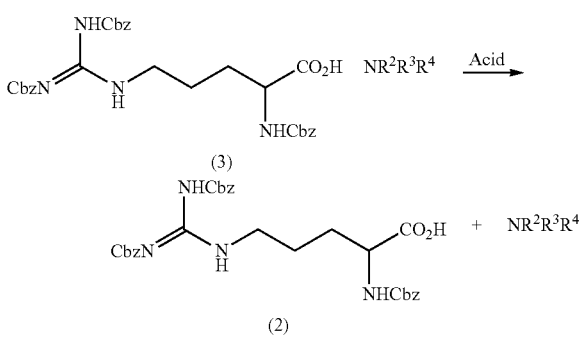

The present invention is characterized in that a tri-carbobenzoxy-arginine is produced by extracting a tri-carbobenzoxy-arginine amine salt in an organic solvent using an acid in an organic solvent or a water/organic solvent bilayer system. The tri-carbobenzoxy-arginine amine salt preferably comprises a solid obtained in "Production of tri-carbobenzoxy-arginine amine salt" as described above, and the solid is dissolved in an organic solvent or a water/organic solvent bilayer system using an acid, and then extracted in an organic solvent. By repeatedly carrying out the above-mentioned method for producing a tri-carbobenzoxy-arginine amine salt and the method for producing a tri-carbobenzoxy-arginine, the tri-carbobenzoxy-arginine can be refined, so that a tri-carbobenzoxy-arginine having a high purity can be obtained.

The organic solvent to be used in the extraction is not particularly limited, and examples thereof include acetic acid esters such as ethyl acetate, n-propyl acetate, isopropyl acetate, n-butyl acetate, isobutyl acetate and tert-butyl acetate; ethers such as tert-butyl methyl ether and ethylene glycol dibutyl ether; halogenated hydrocarbons such as dichloromethane, chloroform and 1,2-dichloroethane; and aromatic hydrocarbons such as toluene, chlorobenzene and xylene. Tert-butyl methyl ether, dichloromethane, toluene and ethyl acetate are more preferable. It is needless to say that these organic solvents may be used alone, or used in combination of two or more thereof.

The amount of water to be used in the extraction is not particularly limited, and it may be such an amount that a salt of an acid to be added in extraction and an amine is dissolved.

The upper limit of the amount of the organic solvent to be used in the extraction is not particularly limited, but for example, it is 40 parts by weight, preferably 20 parts by weight, more preferably 10 parts by weight with respect to 1 part by weight of the tri-carbobenzoxy-arginine amine salt. The lower limit of the amount of the organic solvent is not particularly limited, but for example, it is 1 part by weight, preferably 3 parts by weight, more preferably 5 parts by weight with respect to 1 part by weight of the tri-carbobenzoxy-arginine amine salt.

Examples of the acid to be used for acidification in the extraction include mineral acids, sulfonic acids and carboxylic acids. The mineral acid is not particularly limited, and examples thereof include aqueous solutions of hydrogen halides such as hydrogen chloride and hydrogen bromide (hydrochloric acid, hydrobromic acid and the like), sulfuric acid and phosphoric acid. The sulfonic acid is not particularly limited, and examples thereof include methanesulfonic acid, ethanesulfonic acid, propanesulfonic acid, butanesulfonic acid, benzenesulfonic acid, p-toluenesulfonic acid, camphorsulfonic acid and 1-phenylethanesulfonic acid. The carboxylic acid is not particularly limited, and examples thereof include non-optically-active carboxylic acids such as formic acid, acetic acid, trifluoroacetic acid and benzoic acid, and optically active carboxylic acids such as tartaric acid. Among these acids, preferable are hydrogen chloride, hydrogen bromide, p-toluenesulfonic acid and benzoic acid, particularly hydrogen chloride, hydrogen bromide and sulfuric acid, with hydrogen chloride and sulfuric acid being especially preferable.

The temperature in addition of the acid and the temperature in extraction are not particularly limited, and the addition and extraction can be performed at a temperature that is high enough to prevent the reaction solvent from being solidified. The upper limit of the temperature is not particularly limited, but it is 100° C., preferably 70° C., more preferably 50° C. The lower limit of the temperature is not particularly limited, but it is −50° C., preferably −30° C., more preferably −10° C.

The purity of the obtained tri-carbobenzoxy-arginine as measured by high-performance liquid chromatography is, for example, not less than 80 area %, preferably not less than 85 area %, more preferably not less than 90 area %, and even a purity of 99.9 area % can be obtained.

The present application claims the benefit of priority with respect to Japanese Patent Application No. 2014-68838 filed in Mar. 28, 2014. Japanese Patent Application No. 2014-68838 filed in Mar. 28, 2014 is incorporated herein by reference in its entirety.

EXAMPLES

Hereinafter, the present invention will be described further in detail by way of examples, but the present invention is in no way limited to these examples as a matter of course.

In examples, the yield and generation ratio of each compound were analyzed by high-performance liquid chromatography. The purity (area %) refers to the area of the peak of an object with respect to the total peak area after subtracting peak shapes resulting from solvent peaks and system-originated wavelength disturbances (hereinafter, referred to as a "blank").

In examples, the yield and generation ratio of each compound were analyzed by high-performance liquid chromatography under the conditions described below.
[High-Performance Liquid Chromatography Analysis Conditions]
Column: Zorbax Eclipse Plus C18, 50×4.6 mm; 1.8 μm
Mobile phase A: 0.1 wt % phosphoric acid aqueous solution,
Mobile phase B: acetonitrile
Flow rate: 1.0 mL/min

[Gradient Conditions]

| | |
|---|---|
| 0.00 minute | mobile phase A:mobile phase B = 90:10 |
| 15.00 minutes | mobile phase A:mobile phase B = 10:90 |
| 25.00 minutes | mobile phase A:mobile phase B = 10:90 |
| 25.01 minutes | mobile phase A:mobile phase B = 90:10 |
| 30.00 minutes | STOP |

Column temperature: 40 degrees
Detected wavelength: 210 nm

Comparative Example 1

Method for Producing Tri-Carbobenzoxy-Arginine Sodium Salt

1 N NaOH aqueous solution (1.72 mL, 1.72 mmol, 1.0 eq) was added to D-arginine (300 mg, 1.72 mmol) to dissolve the D-arginine, and the solution was then cooled to an internal temperature of 0° C. 2 N NaOH aqueous solution (0.86 mL, 1.72 mmol, 1.0 eq) and carbobenzoxy chloride (293 mg, 1.72 mmol, 1.0 eq) were alternately added five times for 0.5 hours. A solid was precipitated to form an aggregate at the end of second addition, and stirring was no longer possible at the end of addition of the total amount. The reaction liquid was filtered by a Kiriyama funnel. The liquid was very poor in filtration characteristic (about 1 hour with a 21 mm Kiriyama funnel). The wet solid was vacuum-dried to obtain a tri-carbobenzoxy-arginine sodium salt dry solid (149 mg, 0.258 mmol, yield 15.0%).

Comparative Example 2

Method for Producing Tri-Carbobenzoxy-Arginine Sodium Salt

Water (50.00 g) and 30% KOH aqueous solution (21.47 g, 114.8 mmol, 1.0 eq) were added to L-arginine (20.00 g, 114.8 mmol) to dissolve the L-arginine, and the solution was then cooled to an internal temperature of 0° C. 30% KOH aqueous solution (21.47 g, 114.8 mmol, 1.0 eq) and carbobenzoxy chloride (19.58 g, 114.8 mmol, 1.0 eq) were alternately added five times for 4.5 hours. A solid was precipitated to form an aggregate at the end of second addition, and stirring was no longer possible at the end of addition of the total amount as with Comparative Example 1.

Example 1

Method for Producing Tri-Carbobenzoxy-Arginine (2)

D-arginine hydrochloride (10 g, 47.47 mmol), sodium 1-octanesulfonate (3.10 g, 14.3 mmol, 0.30 eq) and H$_2$O (10.00 g) were mixed, and the mixture was then cooled to an internal temperature of 0° C. 10% KOH aqueous solution (53.27 g, 94.94 mmol, 2.0 eq) and tert-butyl methyl ether (50.00 g) were added. Carbobenzoxy chloride (32.40 g, 189.9 mmol, 4.0 eq) and 10% KOH aqueous solution (159.81 g, 284.8 mmol, 6.0 eq) were simultaneously added for 5 hours (first addition) (at this time, the ratio of a mono-carbobenzoxy-arginine was 10.9 area % and the ratio of a di-carbobenzoxy-arginine was 96.7 area % with respect to 100 area % of a tri-carbobenzoxy-arginine).

Subsequently, temperature control was performed so that the internal temperature was 15° C., and carbobenzoxy chloride (21.87 g, 128.2 mmol, 2.7 eq) and 10% KOH aqueous solution (98.55 g, 175.6 mmol, 3.7 eq) were then simultaneously added for 15 hours while being kept at a pH of 11 to 12 (second addition) (at this time, the ratio of the mono-carbobenzoxy-arginine was 1.3 area % and the ratio of the di-carbobenzoxy-arginine was 4.3 area %). The reaction liquid had satisfactory fluidity all the time, and was thus successfully stirred. After completion of the reaction, 35% hydrochloric acid (22.06 g, 211.8 mmol, 4.5 eq) was added to adjust the pH to 1.1. The organic layer was washed with H$_2$O (30 g) twice to obtain a tri-carbobenzoxy-arginine organic layer (144.46 g, pure content 16.0 g, 27.7 mmol, yield 58.4%, 31.3 area %).

Example 2

Tert-butyl methyl ether (81.00 g) was added to the tri-carbobenzoxy-arginine organic layer (139.42 g, pure content 15.46 g, 26.81 mmol, 31.3 area %) obtained in Example 1, and dicyclohexylamine (7.29 g, 40.2 mmol, 1.5 eq) was then added for 2 hours to precipitate a tri-carbobenzoxy-arginine dicyclohexyl amine salt. The solid had a very good filtration characteristic (about 5 minutes with a 60 mm Kiriyama funnel). The solid was washed with tert-butyl methyl ether (70.00 g) to obtain a tri-carbobenzoxy-arginine dicyclohexyl amine salt wet solid (18.72 g, 91.0 area %).

Water (106.38 g) and ethyl acetate (159.57 g) were added to the obtained tri-carbobenzoxy-arginine dicyclohexyl amine salt wet solid (17.73 g, 91.0 area %), and the mixture was cooled to an internal temperature of 0° C. 97% H$_2$SO$_4$ (1.3 g, 12.9 mmol) was added to adjust the pH to 1.7. The aqueous layer was removed, and the organic layer was then washed with water (106.00 g) to obtain a tri-carbobenzoxy-arginine organic layer (163.89 g, pure content 12.40 g, 21.51 mmol, yield 84.7%, 90.5 area %).

Examples 3 to 12

The same procedure as in Example 1 was carried out to perform carbobenzoxylation of an arginine under the conditions shown in Table 1. The organic solvent/water ratio in the reaction solvent is the same as in Example 1 (water mentioned here is only added water, and does not include water derived from the KOH aqueous solution). Reaction yields are shown in Table 1.

Examples 13 to 20

In Examples 14 to 17, the same procedure as in Example 2 was carried out to obtain a high-purity tri-carbobenzoxy-arginine solution from a tri-carbobenzoxy-arginine reaction organic layer under the conditions shown in Table 2. In Examples 13 and 18 to 20, a tri-carbobenzoxy-arginine solution was repeatedly refined to obtain a further high-purity tri-carbobenzoxy-arginine solution under the conditions shown in Table 2.

Example 21

The tri-carbobenzoxy-arginine solution obtained in Example 14 was concentrated at a jacket temperature of 40° C. and a pressure of 10 mmHg for 1 hour, and then vacuum-dried at a jacket temperature of 40° C. for 12 hours to obtain a tri-carbobenzoxy-arginine (89.1 wt %, 92.7 area %).

TABLE 1

| | | | Base | | | | Carbobenzoxy |
| --- | --- | --- | --- | --- | --- | --- | --- |
| | Raw material | Reaction solvent | Initial stage | First addition | Second addition | Total | First addition |
| Example 1 | D-arginine hydrochloride | t-Butyl methyl ether/water = 5/1 (weight ratio) | 10% KOH (2.0 parts by mol) | 10% KOH (6.0 parts by mol) | 10% KOH (3.7 parts by mol) | 10% KOH (11.7 parts by mol) | 4.0 parts by mol |
| Example 3 | L-arginine | t-Butyl methyl ether/water = 2/1 (weight ratio) | 10% KOH (1.0 part by mol) | 10% KOH (5.6 parts by mol) | 10% KOH (3.0 parts by mol) | 10% KOH (9.6 parts by mol) | 4.0 parts by mol |
| Example 4 | L-arginine | t-Butyl methyl ether/water = 2/1 (weight ratio) | 10% KOH (3.0 part by mol) | 10% KOH (4.7 parts by mol) | 10% KOH (2.3 parts by mol) | 10% KOH (8.0 parts by mol) | 4.0 parts by mol |
| Example 5 | D-arginine hydrochloride | t-Bulyl methyl ether/water = 1/1 (weight ratio) | 30% KOH (3.0 parts by mol) | 30% KOH (5.7 parts by mol) | 30% KOH (3.4 parts by mol) | 30% KOH (12.1 parts by mol) | 4.5 parts by mol |
| Example 6 | D-arginine hydrochloride | Dichloromethane/water = 1/1 (weight ratio) | 30% KOH (3.0 parts by mol) | 30% KOH (4.2 parts by mol) | 30% KOH (— part(s) by mol) | 30% KOH (7.2 parts by mol) | 4.5 parts by mol |
| Example 7 | L-arginine | t-Butyl methyl ether/water = 1/1 (weight ratio) | 30% KOH (2.0 parts by mol) | 30% KOH (4.8 parts by mol) | 30% KOH (2.1 parts by mol) | 30% KOH (8.9 parts by mol) | 4.0 parts by mol |
| Example 8 | L-arginine | Dichloromethane/water = 1/1 (weight ratio) | 30% KOH (1.0 part by mol) | 30% KOH (3.0 parts by mol) | 30% KOH (— part(s) by mol) | 30% KOH (4.0 parts by mol) | 3.0 parts by moll |
| Example 9 | L-arginine | Toluene/water = 4/1 (weight ratio) | 30% KOH (2.0 parts by mol) | 30% KOH (11.6 parts by mol) | 30% KOH (— part(s) by mol) | 30% KOH (13.6 parts by mol) | 7.0 parts by mol |
| Example 10 | L-arginine | Dichloromethane/water = 2/1 (weight ratio) | 10% NaOH (1.0 part by mol) | 10% NaOH (5.5 parts by mol) | 10% NaOH (— part(s) by mol) | 10% NaOH (6.5 parts by mol) | 5.0 parts by mol |
| Example 11 | L-arginine | Dichloromethane/water = 4/1 (weight ratio) | 10% KOH (1.0 part by mol) | 10% KOH (6.0 parts by mol) | 10% KOH (— part(s) by mol) | 10% KOH (7.0 parts by mol) | 5.5 parts by mol |
| Example 12 | L-arginine | t-Butyl methyl ether/water = 1/1 (weight ratio) | 30% KOH (2.0 parts by mol) | 30% KOH (8.3 parts by mol) | 30% KOH (— part(s) by mol) | 30% KOH (10.3 parts by mol) | 7.5 parts by mol |

TABLE 1-continued

| | Carbobenzoxy | | Surfactant | HPLC analysis | | Carbobenzoxylation |
| --- | --- | --- | --- | --- | --- | --- |
| | Second addition | Total | (parts by mol) | After first addition | After second addition | reaction yield |
| Example 1 | 2.7 parts by mol | 6.7 parts by mol | Sodium 1-octanesulfonate (0.30 parts by mol) | Monosubstituted: 5.2% Disubstituted: 46.6% Trisubstituted: 48.2% | Monosubstituted: 1.2% Disubstituted: 4.1% Trisubstituted: 94.7% | 58.4 |
| Example 3 | 2.0 parts by mol | 6.0 parts by mol | Sodium 1-octanesulfonate (0.25 parts by mo1) | Monosubstituted: 2.4% Disubstituted: 45.6% Trisubstituted: 52.0% | Monosubstituted: 0.9% Disubstituted: 0.9% Trisubstituted: 98.2% | 57.2 |
| Example 4 | 2.0 parts by mol | 6.0 parts by mol | Sodium 1-octanesulfonate (0.30 parts by mol) | Monosubstituted: 3.9% Disubstituted: 34.9% Trisubstituted: 61.2% | Monosubstituted: 1.3% Disubstituted: 7.0% Trisubstituted: 91.7% | 68.5 |
| Example 5 | 2.0 parts by mol | 6.5 parts by mol | Sodium 1-octanesulfonate (0.25 parts by mol) | Monosubstituted: 1.1% Disubstituted: 47.8% Trisubstituted: 51.1%) | Monosubstituted: 0.5% Disubstituted: 4.8% Trisubstituted: 94.7% | 47.4 |
| Example 6 | — part(s) by mol | 4.5 parts by mol | None | Monosubstituted: — % Disubstituted: — % Trisubstituted: — % | Monosubstituted: — % Disubstituted: — % Trisubstituted: — % | 34.1 |
| Example 7 | 1.5 parts by mol | 5.5 parts by mol | Sodium 1-heptanesulfonate (0.25 parts by mol) | Monosubstituted: 2.2% Disubstituted: 48.7% Trisubstituted: 49.1% | Monosubstituted: 2.7% Disubstituted: 3.3% Trisubstituted: 94.0% | 54.3 |
| Example 8 | — part(s) by mol | 3.0 parts by mol | None | Monosubstituted: — % Disubstituted: — % Trisubstituted: — % | Monosubstituted: — % Disubstituted: — % Trisubstituted: — % | 36.3 |
| Example 9 | — part(s) by mol | 7.0 parts by mol | None | Monosubstituted: — % Disubstituted: — % Trisubstituted: — % | Monosubstituted: — % Disubstituted: — % Trisublituted: — % | 41.4 |
| Example 10 | — part(s) by mol | 5.0 parts by mol | None | Monosubstituted: — % Disubstituted: — % Trisubstituted: — % | Monosubstituted: — % Disubstituted: — % Trisubstituted: — % | 35.1 |
| Example 11 | — part(s) by mol | 5.5 parts by mol | None | Monosubstituted: — % Disubstituted: — % Trisubstituted: — % | Monosubstituted: — % Disubstituted: — % Trisubstituted: — % | 44.0 |
| Example 12 | — part(s) by mol | 7.5 parts by mol | Sodium 1-heptanesulfonate (0.30 parts by mol) | Monosubstituted: — % Disubstituted: — % Trisubstituted: — % | Monosubstituted: — % Disubstituted: — % Trisubstituted: — % | 61.6 |

TABLE 2

| | Origin | Quality of tri-carbobenzoxy-arginine solution before refinement (area %)* | Dicyclo-hexylamine (mol) | Amine salt purity (area %)* | Acid in extraction | Solidification-extraction yield (%) | Quality of tri-carbobenzoxy-arginine solution after refinement (area %)* |
| --- | --- | --- | --- | --- | --- | --- | --- |
| Example 2 | Example 1 Reaction organic layer | 31.3 area % | 1.5 parts by mol | 91.0 area % | 97% $H_2SO_4$ | 84.7% | 90.5 area % |
| Example 13 | Example 2 After refinement Tri-carbobenzoxy-arginine solution | 90.5 area % | 1.0 part by mol | 98.4 area % | 97% $H_2SO_4$ | 92.5% | 98.5 area % |
| Example 14 | Example 3 Reaction organic layer | 36.4 area % | 1.5 parts by mol | 92.1 area % | 55% $H_2SO_4$ | 93.3% | 93.1 area % |
| Example 15 | Example 5 Reaction organic layer | 26.8 area % | 2.0 parts by mol | 90.6 area % | 55% $H_2SO_4$ | 92.9% | 91.4 area % |
| Example 16 | Example 6 Reaction organic layer | 26.9 area % | 1.5 parts by mol | 88.5 area % | 35% HCl | 89.5% | 91.4 area % |
| Example 17 | Example 6 Reaction organic layer | 26.9 area % | 1.2 parts by mol | 92 area % | 55% $H_2SO_4$ | 96.2% | 91.6 area % |
| Example 18 | Example 15 After refinement Tri-carbobenzoxy-arginine solution | 91.4 area % | 1.5 parts by mol | 97.1 area % | 55% $H_2SO_4$ | 100.0% | 96.5 area % |
| Example 19 | Example 18 After refinement Tri-carbobenzoxy-arginine solution | 96.5 area % | 1.5 parts by mol | 97.7 area % | 55% $H_2SO_4$ | 92.9% | 97.9 area % |

TABLE 2-continued

| Origin | | Quality of tri-carbobenzoxy-arginine solution before refinement (area %)* | Dicyclo-hexylamine (mol) | Amine salt purity (area %)* | Acid in extraction | Solidification-extraction yield (%) | Quality of tri-carbobenzoxy-arginine solution after refinement (area %)* |
|---|---|---|---|---|---|---|---|
| Example 20 | Example 19 After refinement Tri-carbobenzoxy-arginine solution | 97.9 area % | 1.0 part by mol | 98.9 area % | 55% H₂SO₄ | 93.2% | 99.1 area % |

*Area % of tri-carbobenzoxy-arginine with respect to peak total area after subtracting blank originating from solvent and system

INDUSTRIAL APPLICABILITY

The present invention can be used for production of peptides.

The invention claimed is:

1. A method for producing a tri-carbobenzoxy-arginine of the formula

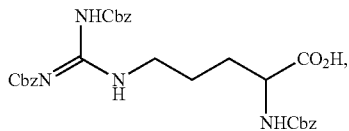
(2)

wherein Cbz represents a benzyloxycarbonyl group,
the method comprising:
adding carbobenzoxy chloride and a base in the presence of a surfactant to an arginine or arginine derivative of the formula (1) or a salt thereof:

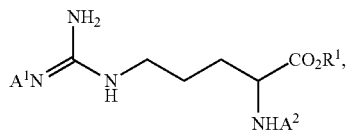
(1)

wherein $A^1$ and $A^2$ each represents an amino group protecting group or a hydrogen atom, and $R^1$ represents a hydrogen atom, an alkyl group having 1 to 6 carbon atoms optionally having a substituent, or an aralkyl group having 7 to 15 carbon atoms optionally having a substituent, such that the arginine or arginine derivative of the formula (1) or a salt thereof is carbobenzoxylated,
wherein, in the adding, the carbobenzoxy chloride and the base are added to the arginine or arginine derivative of the formula (1) or a salt thereof in a bilayer system comprising water and an organic solvent, and
wherein the surfactant is selected from the group consisting of a carboxylic acid-type surfactant, a sulfonic acid-type surfactant, a sulfuric acid ester-type surfactant, a phosphoric acid ester-type surfactant and a quaternary ammonium salt-type surfactant.

2. The method according to claim 1, wherein the base is an alkali metal hydroxide.

3. The method according to claim 1, wherein the arginine or arginine derivative of the formula (1) is an arginine or arginine hydrochloride.

4. The method according to claim 1, further comprising: deprotecting and carbobenzoxylating the amino group protecting group of $A^1$ or $A^2$.

5. A method for producing a tri-carbobenzoxy-arginine amine salt of the formula (3) in a solid form,

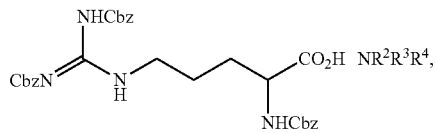
(3)

wherein $R^2$, $R^3$ and $R^4$ each represents a hydrogen atom, an alkyl group having 1 to 6 carbon atoms optionally having a substituent, or an aralkyl group having 7 to 15 carbon atoms optionally having a substituent,
the method comprising:
producing a tri-carbobenzoxy-arginine by the method according to claim 1; and
adding an amine to a solution comprising the tri-carbobenzoxy-arginine such that the tri-carbobenzoxy-arginine amine salt in a solid form is obtained.

6. A method for producing a tri-carbobenzoxy-arginine, comprising:
producing a tri-carbobenzoxy-arginine amine salt in a solid form by the method according to claim 5; and
adding an acid to the tri-carbobenzoxy-arginine amine to extract a tri-carbobenzoxy-arginine in an organic layer.

7. The method according to claim 1, wherein $A^1$ and $A^2$ in the formula (1) each is a hydrogen atom.

8. The method according to claim 1, wherein the organic solvent comprises at least one selected from the group consisting of ethyl acetate, n-propyl acetate, isopropyl acetate, n-butyl acetate, isobutyl acetate, tert-butyl acetate, tert-butyl methyl ether, ethylene glycol dibutyl ether, dichloromethane, chloroform, 1,2-dichloroethane, toluene, chlorobenzene, and xylene.

9. The method according to claim 1, wherein the bilayer system comprises from 1 to 10 parts by weight of water with respect to 1 part by weight of the organic solvent.

10. The method according to claim 1, wherein, in the adding, 32 mol or less of the carbobenzoxy chloride is added with respect to 1 mol of the arginine or arginine derivative of the formula (1) or a salt thereof.

11. The method according to claim 1, wherein the adding comprises simultaneously and continuously adding the carbobenzoxy chloride and the base to the arginine or arginine derivative of the formula (1) or a salt thereof.

12. The method according to claim 1, wherein, in the adding, the carbobenzoxy chloride and the base are added such that the arginine or arginine derivative of the formula (1) or a salt thereof is carbobenzoxylated at a temperature of from −50° C. to 50° C.

13. A method for producing a tri-carbobenzoxy-arginine, comprising:

producing a tri-carbobenzoxy-arginine amine salt of the formula (3) in a solid form

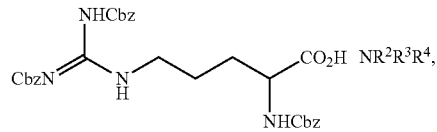

(3)

wherein $R^2$, $R^3$ and $R^4$ each represents a hydrogen atom, an alkyl group having 1 to 6 carbon atoms optionally having a substituent, or an aralkyl group having 7 to 15 carbon atoms optionally having a substituent, by the following method comprising:

adding an amine to a tri-carbobenzoxy-arginine of the formula (2):

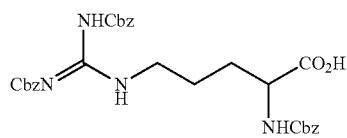

(2)

such that the tri-carbobenzoxy-arginine amine salt is obtained, and isolating the obtained tri-carbobenzoxy-arginine amine salt, and adding an acid to the tri-carbobenzoxy-arginine amine salt to extract a tri-carbobenzoxy-arginine in an organic layer.

14. A method for producing a tri-carbobenzoxy-arginine, comprising:

producing a tri-carbobenzoxy-arginine amine salt of the formula (3) in a solid form,

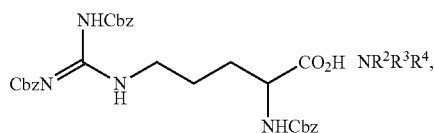

(3)

wherein $R^2$, $R^3$ and $R^4$ each is a hydrogen atom, an alkyl group having 1 to 6 carbon atoms optionally having a substituent, or an aralkyl group having 7 to 15 carbon atoms optionally having a substituent, by the following the method comprising:

adding an amine to a tri-carbobenzoxy-arginine of the formula (2):

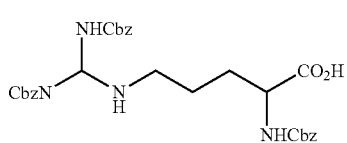

(2)

such that the tri-carbobenzoxy-arginine amine salt is obtained, and filtering the obtained tri-carbobenzoxy-arginine amine salt, and adding an acid to the tri-carbobenzoxy-arginine amine salt to extract a tri-carbobenzoxy-arginine in an organic layer.

* * * * *